US006666845B2

(12) United States Patent
Hooper et al.

(10) Patent No.: US 6,666,845 B2
(45) Date of Patent: Dec. 23, 2003

(54) IMPLANTABLE INFUSION PUMP

(75) Inventors: Sandra Marie Hooper, Allen, TX (US); Bruce David Wigness, Minneapolis, MN (US); Brian Russell Blischak, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 147 days.

(21) Appl. No.: 09/755,894

(22) Filed: Jan. 4, 2001

(65) Prior Publication Data
US 2002/0087147 A1 Jul. 4, 2002

(51) Int. Cl.[7] ............................................. A61M 37/00
(52) U.S. Cl. ..................................... 604/132; 604/892.1
(58) Field of Search ......................... 604/892.1, 890.1, 604/93, 174, 175, 247, 891.1

(56) References Cited

U.S. PATENT DOCUMENTS

| 3,731,681 A | 5/1973 | Blackshear et al. ...... 128/214 F |
| 3,951,147 A | 4/1976 | Tucker et al. ............... 128/260 |
| 4,604,090 A | * 8/1986 | Reinicke ...................... 604/118 |
| 4,699,615 A | * 10/1987 | Fischell et al. ............. 604/131 |
| 4,772,263 A | 9/1988 | Dorman et al. ............. 604/132 |
| 5,045,064 A | 9/1991 | Idriss |
| 5,527,307 A | * 6/1996 | Srisathapat et al. ...... 604/892.1 |

FOREIGN PATENT DOCUMENTS

| EP | 0335671 | 10/1989 |
| EP | 0450186 A1 | 10/1991 |
| WO | WO 84/01718 | 5/1984 |

* cited by examiner

Primary Examiner—Manuel Mendez
(74) Attorney, Agent, or Firm—Fulbright & Jaworski L.L.P.

(57) ABSTRACT

An implantable infusion pump to deliver stored infusate to a desired fluid delivery site. The pump includes a collapsible fluid chamber. The pump can include a multi-stage filtration system to filter micro-emboli as well as larger particles that are inadvertently introduced into the pump system. An external member can receive the pump and provide a medium to include additional, interactive components, e.g., a bolus port, as well as provide a versatile suture structure to enable the pump to be properly secured within an implantation site. To improve volumetric efficiency, the pump can further incorporate an outlet flow passage within a movable wall of the fluid chamber.

30 Claims, 7 Drawing Sheets

IMPLANTABLE INFUSION PUMP

TECHNICAL FIELD OF THE INVENTION

The present invention concerns an implantable infusion pump, and in particular, an implantable infusion pump as well as independent components therefor that enable securing the pump within a living body, multi-stage filtration, and protection of a fluid-delivery catheter in and about the pump housing while improving volumetric efficiency of the pump configuration.

BACKGROUND OF THE INVENTION

The present invention relates to an implantable infusion pump for infusing drugs or other chemicals or solutions into a body wherein the infusion pump is implanted. Further, in at least one embodiment, the present invention relates to an implantable infusion pump that compensates for changes in both ambient pressure and ambient temperature so as to accurately control the flow rate of infusates from the implantable infusion pump into the body.

Infusion pump designs were rarely seen in medical literature until the 1950s. Most of these early infusion pumps were extracorporeal devices of various designs. One such device included a reciprocating air pump driven by an electric motor. Yet another design considered comprised a metal housing for a glass syringe and a compression chamber fed by a tank of nitrogen gas. Yet another such infusion pump included a motorized syringe pump which included an electric motor connected to the worm drive that moved a syringe plunger by a gear box. The gears were interchangeable such that replacement of the gears permitted different delivery rates. Yet another infusion pump included a syringe plunger driven by a rider on a threaded shaft. While this is but a sampling of such devices, it should be appreciated that numerous other designs were considered and used for extracorporeal infusion devices.

Modern constant-flow implantable infusion devices, or implantable pumps, for delivering an infusate (e.g., medicaments, insulin, etc.) commonly have a rigid housing that maintains a collapsible infusate reservoir. The housing includes a needle-penetrable septum that covers a reservoir inlet. A flow passage is provided between the reservoir and an exterior surface of the device, such flow passage includes, or defines, a restrictor to establish a maximum output infusate flow rate. At the flow passage outlet, a flexible delivery catheter is provided.

Practically, such a device is implanted at a selected location in a body so that (i) the inlet septum is proximate to the patient's skin and (ii) a distal end of the catheter is positioned at a selected delivery site. Infusate can then be delivered to the infusion site by forcing such fluid from the device reservoir. When the infusate reservoir becomes empty, the reservoir is refillable through the septum inlet by injecting a new supply of infusate through the apparatus' inlet septum. Due to the location of the device in relation to the skin of the patient, injection can be readily accomplished using a hypodermic needle (or cannula).

Infusate is expelled from the reservoir to an infusion site by collapsing the reservoir. While some infusion pumps use an electrically powered mechanism to force infusate from the reservoir, other such devices commonly use a two-phase fluid, or propellant, that is contained within the rigid housing and is further confined within a fluid-tight space adjacent to the infusate reservoir.

The propellant is both a liquid and a vapor at patient physiological temperatures, e.g., 98.6° F., and theoretically exerts a positive, constant pressure over a full volume change of the reservoir, thus effecting the delivery of a constant flow of infusate. More particularly, when the infusate reservoir is expanded upon being refilled, the propellant is compressed, where a portion of such vapor reverts to its liquid phase and thereby recharges the vapor pressure power source of the pump. The construction and operation of implantable infusion pumps of this type are described in detail, for example, in U.S. Pat. Nos. 3,731,681 and 3,951,147.

Gas-driven infusion pumps typically provide a cost-effective means to deliver a consistent flow of infusate throughout a delivery cycle. Notwithstanding, the rigid housing of the gas-driven infusion pump allows both environmental temperature and atmospheric pressure to affect an output fluid flow. With some drugs, particularly those having small therapeutic indices, such changes in drug infusion rates are undesirable and, in certain situations, unacceptable.

Circumstances readily exist where either environmental temperature or pressure can rapidly change a significant amount. For example, in regard to temperature, an internalized pump pressure can change as much as 0.5 psi for each 1° F. change in body temperature. Thus, for example, assuming a pump driving force of 8 psi at 98.6° F., a twenty-five percent (25%) increase in pressure and drug flow rate can result from a fever of only 102.6° F.

An even more serious situation results from changes in atmospheric pressure. Although minor variations in atmospheric pressure at any given location on earth does not significantly affect delivery flow rates, with modern modes of transportation, a patient can rapidly change altitude during travel, such as when traveling in the mountains or when traveling by plane.

Again, the rigid housing of the conventional, gas-driven infusion pump is intended to produce a constant internal pressure (at constant temperature) independent of the external pressure. Largely due to compliance by the lungs and venous circulatory system, hydrostatic pressure within the human body closely follows atmospheric pressure. The net effect is a pressure differential across the fluid flow restrictor of infusion pump (typically a capillary tube or the like) which changes linearly with external pressure. Consequently, a delivered infusate flow rate can increase as much as forty percent (40%) when a patient takes a common commercial airline flight.

A viable solution to address changes in atmospheric conditions for constant-flow infusion pumps is disclosed in U.S. Pat. No. 4,772,263, herein incorporated by reference in its entirety. Specifically, in place of the conventional rigid enclosure that maintains a two-phase fluid, the disclosure teaches forming the fluid reservoir between a rigid portion (which maintains at least the inlet septum and the restrictor) and a flexible drive-spring diaphragm. The diaphragm is exposed to the body of the patient and "senses" internal body pressure so as to compensate for changes in the internal body pressure caused by changes in atmospheric pressure and temperature.

While the disclosure of U.S. Pat. No. 4,772,263 provides a foundational description for a pump having a drive-spring diaphragm capable of constant-flow delivery, such patent does not fully consider alternatives for restrictor and/or flow passage outlet placement that may provide for a safer practical configuration as well as capitalize on the unique structure of the drive-spring diaphragm.

Moreover, U.S. Pat. No. 4,772,263 is silent to a means to incorporate a conventional bolus port with its unique drive-spring diaphragm design. A bolus port enables direct infusion of a fluid through the delivery catheter. A bolus port is typically a separate septum that is in fluid communication with an outlet of an associated infusion pump and a delivery catheter therefor. Typically, certain one-way valving structures can prevent fluid that is injected through the bolus port from-flowing upstream to the infusate reservoir of the infusion pump.

SUMMARY OF THE INVENTION

The present invention relates to an infusion pump for implantation in a living body. The infusion pump includes a housing having a fluid chamber, wherein the housing includes a spring-energy source for driving an infusate (e.g., medicaments, insulin, etc.) out of the fluid chamber and compensating for changes in internal body pressure and/or internal body temperature. The housing further includes an inlet conduit in communication with the fluid chamber and an outlet conduit in communication with the fluid chamber that leads to an infusion site in the body. A self-sealing, penetrable member is provided in the inlet conduit to facilitate periodic refilling of the drug chamber when the infusion pump is implanted. The spring-energy source allows a pressure differential between the fluid chamber and the internal body pressure to remain constant and unaffected by changes in body temperature or atmospheric pressure.

In accordance with one aspect of the present invention, the 'spring-energy source is a spring diaphragm that forms a flexible, exterior rear wall of the fluid chamber that operatively applies pressure on a fluid solution stored in the fluid chamber equivalent to a predetermined constant force collectively exerted by the spring diaphragm and an internal body pressure of the patient.

In accordance with another aspect of the present invention, an infusion pump for implantation in a living body has a variable-volume fluid chamber, a housing, and a driving spring. An inlet conduit of the pump includes a self-sealing penetrable member and extends between a surface of the housing and the fluid chamber. An outlet conduit of the pump communicates with the fluid chamber and is connectable to a delivery catheter. In addition to the driving spring being adapted to supply a principle force to drive a fluid stored in the fluid chamber into the body, the driving spring also includes the outlet conduit, which enters, passes through, and exits the driving spring.

Another aspect of the present invention is directed to an implantable pump having a housing, an outlet conduit, and a multi-stage filter system. The housing defines a variable-volume fluid chamber to store infusate. The outlet conduit is in communication with the fluid chamber and connectable to a delivery catheter. The multi-stage filter system, positioned within the outlet conduit, filters infusate prior to delivery via the delivery catheter.

Another aspect of the present invention is directed to an implantable pump that includes a housing having both a collapsible fluid chamber to store infusate and an energy source to collapse the fluid chamber. The pump further includes an inlet conduit and an outlet conduit. The inlet conduit, having a self-sealing penetrable member positioned therein, is located at a first position relative to the housing and in communication with the fluid chamber. The outlet conduit is in communication with the fluid chamber and connectable to a delivery catheter. The pump further includes a member having (i) a first mating surface to receive the housing and (ii) a reinforced-elastomer suture structure, extending substantially about a perimeter of the member, to receive and maintain applied sutures to secure the pump within a living body.

Another aspect of the present invention is directed to an implantable pump that includes a bolus port and a housing having a collapsible fluid chamber to store infusate and an energy source to collapse the fluid chamber. The pump further includes an inlet conduit and an outlet conduit. The inlet conduit, having a self-sealing penetrable member positioned therein, is located at a first position relative to the housing and in communication with the fluid chamber. The outlet conduit is in communication with the fluid chamber. The pump further includes a member having (i) a first mating surface to receive the housing and (ii) a bolus port receptacle, having an inlet and an outlet, to receive the bolus port, wherein the outlet is connectable to a delivery catheter. A connection conduit operatively couples the inlet of the bolus port receptacle and the outlet conduit.

An object of the present invention is to provide an implantable infusion pump having an outlet flow passage that is protected by the upper housing and is removed from potential damage during a refill operation.

Another object of the present invention is to provide an implantable infusion pump having a drive-spring diaphragm with an outlet flow passage that passes through the drive-spring diaphragm.

Another object of the present invention is to provide a suture structure that receives and is attachable to an infusion pump, wherein this structure enables a received infusion pump to be conveniently secured at an implantation site.

Another object of the present invention is to provide a structure that receives and is attachable to an infusion pump and that facilitates a fluid connection between the infusion pump and a bolus port.

Another object of the present invention is to provide a two-stage filtration system for an implantable infusion pump, wherein a first stage functions to filter micro-emboli and a second stage functions to filter greater particulate matter.

Other objects and advantages of the present invention will be apparent to those of ordinary skill in the art having reference to the following specification together with the drawings.

BRIEF DESCRIPTION OF THE DRAWINGS

In the drawings, like reference numerals and letters indicate corresponding parts throughout the several views.

DETAILED DESCRIPTION OF THE PRESENT INVENTION

As a foundation for a detailed description of the present inventions set forth in this disclosure, reference will first be made to that known in the art, and in particular, that generally disclosed in U.S. Pat. No. 4,772,263.

Figure 1:
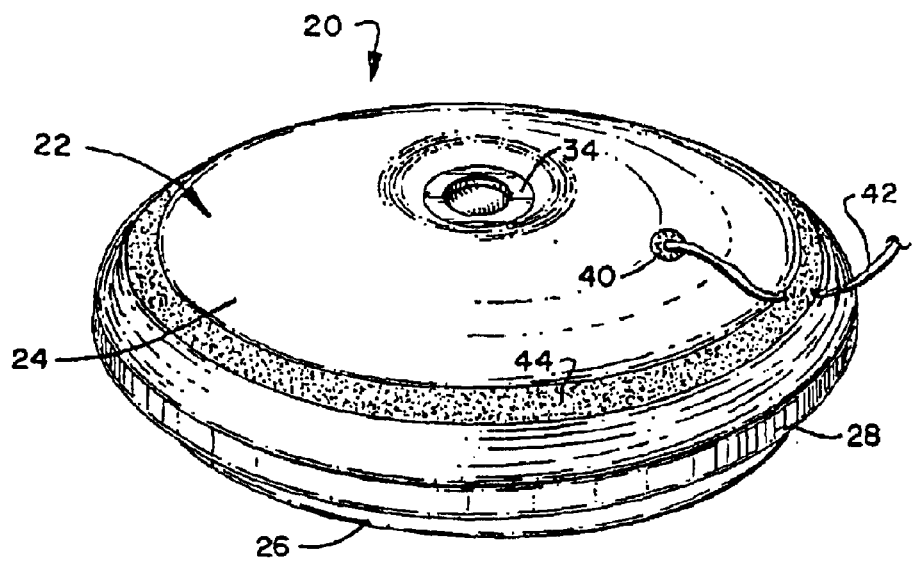
FIG. 1 is a perspective view of a conventional embodiment of a spring-driven infusion pump.
Figure 2:
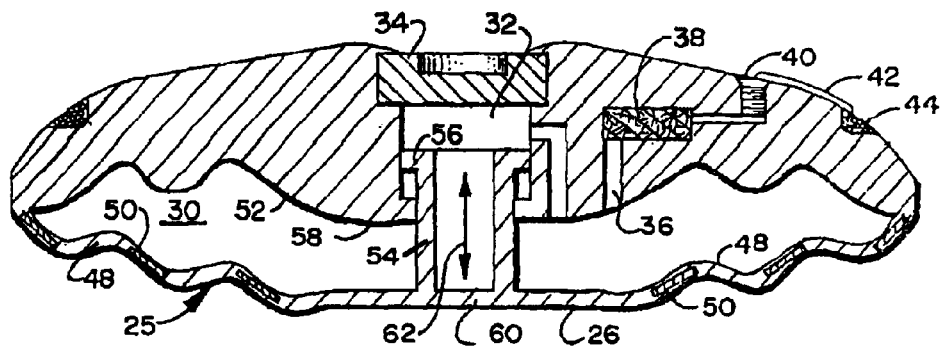
FIG. 2 is a sectional view of the infusion pump shown in FIG. 1, wherein certain portions are being shown diagrammatically.

Referring now to the drawings, there is illustrated in FIGS. 1 and 2 an embodiment of an implantable infusion pump in accordance with at least one aspect of the present invention, the pump being generally designated by the reference numeral 20. The pump 20 has a housing 22 with top and bottom wall portions 24, 26 interconnected by a side wall portion 28 forming a hardened outer shell structure. The expressions "top" and "bottom" are relative and refer only to positions that are generally shown in the drawings.

The top wall portion 24 is constructed of a hardened, non-reactive material, e.g., stainless steel, titanium, etc. In contrast, the bottom wall portion 26 includes a flexible spring diaphragm 25 which cooperates with the remainder of the housing to define a variable-volume, fluid-tight drug chamber 30 for holding insulin, a drug solution or other chemicals or solutions to be infused into an infusion site of a patient's body where the delivery catheter is implanted. The outside surface of the spring diaphragm 25 is exposed to the body and "senses" an internal body pressure so as to compensate for changes in such internal body pressure caused by changes in atmospheric pressure and temperature. The flexible spring diaphragm 25 communicates the internal body pressure to the drug chamber 30.

Notwithstanding the spring diaphragm 25, the infusion pump 20 further includes those features required of an implantable and refillable infusion pump. An inlet conduit 32 extends from the exterior of the housing 22 to the variable-volume, collapsible drug chamber 30 so as to provide for fluid communication from outside the housing 22 to the drug chamber 30. An upper end of the inlet conduit 32 includes a self-sealing, penetrable member or septum 34, suitably positioned therein to provide a fluid-tight seal and yet enable the refilling of the drug chamber 30 by injection. An outlet passage 36 leads from the drug chamber 30 to the exterior of the housing 22 to provide for outflow of drug solution from the drug chamber 30 to the exterior of the housing 22. The outlet passage 36 is illustrated as including a suitable filter 38 for filtering out bacteria and trapped gas, which might be inadvertently introduced into the infusion pump 20 during the manufacturing or the refilling process.

Interconnected to an outer end of the outlet passage 36 by a suitable connector 40 is a flow restrictor 42, or in this instance, capillary tubing, which serves as a flow regulating element. The capillary tubing 42 might be interconnected at an opposite end to a rubber catheter or the like that leads to the site of infusion in the body.

For controlling a rate of delivered flow, the most readily adjustable parameters are (i) the restrictor (i.e., the length and diameter of the capillary) and (ii) the viscosity of the infusate. Addressing the former, the flow rate through the flow restrictor 42 is governed by the Poisseuille equation:

$$Q = (\pi \cdot r^4 \cdot \Delta P)/(8 \cdot \mu \cdot L)$$

where,

Q=flow (ml/sec), r=radius of restrictor passage (cm), $\mu$=viscosity (poise), $\Delta P$=pressure (dynes/cm$^2$), and L=restrictor length (cm).

Several feet of capillary tubing 42 is typically required, for example, 0.5–100 feet, and preferably, 20–100 feet, and more preferably, 50–100 feet.

As illustrated, the capillary tubing 42 might be wrapped about the housing 22 in a groove 44 and suitably secured by a material compatible with body fluids. It will be appreciated that other types of structures or devices might be used to provide for drug output or outflow resistance; for example, spiral groove plate, etched glass, steel capillary tubing, silica chip, etc. Moreover, the resistance elements may number more than one, as in the case of more than one site of infusion.

The outer surface of the top wall portion 24 of the housing 22 is preferably shaped to allow easy identification of the inlet conduit 32 (see also FIG. 5) and suitably protected with a layer of metal or the like to be protected from needle damage during the process of refilling the drug chamber 30. The bottom wall portion 26 and side wall portion 28 might also be similarly protected by a metal layer. As another alternative, the spring diaphragm 25 may include an integrated material (e.g., Kevlarm™ [DuPont Corp., Wilmington, Del.]) to assist in preventing aberrational needle-penetrations during refill operations.

It will be appreciated that the overall design of the infusion pump 20 of the present invention can be more compact and have higher volumetric efficiency than gas-driven pumps since there is no second chamber and the outer shell structure of the infusion pump serves a dual purpose as the infusate-driving energy source and the protective shell.

In the embodiment of the infusion pump shown in FIGS. 1 and 2, the spring diaphragm 25 is formed of a series of nested conical sections 48 interconnected by stiff cylindrical ring sections 50 so as to form a substantially flat spring diaphragm. The conical sections 48 are constructed of an elastomer with a low elastic constant, and the ring sections 50 are preferably constructed of metal with a high elastic constant. The preferred construction technique is to mold the metal ring sections 50 into an elastomer structure forming the conical sections 48. If necessary, the inner surface of the spring diaphragm 25 can be coated with a plastic liner or provided with a thin metal liner to resist drug action on the elastomer and reduce gas diffusion from the body into the drug chamber 30.

Figure 3:
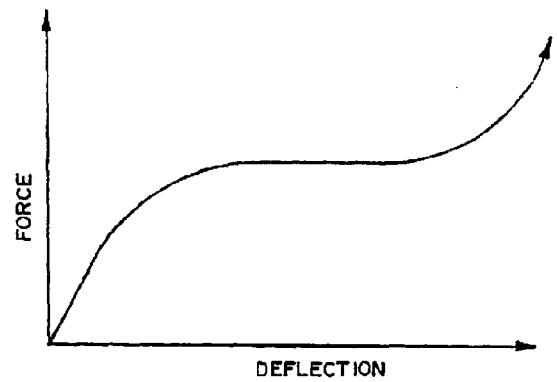
FIG. 3 is a force/deflection curve for the spring-energy source of the present invention, wherein this curve illustrates a constant force over a predetermined range of spring deflection.

This arrangement of conical sections 48 and ring sections 50 provide a spring diaphragm 25 with a useful range of movement or stroke. Moreover, by separating the single conical spring into a nested series of conical sections interconnected by relatively stiff cylindrical ring sections, a substantially flat spring diaphragm having an effective stroke or range of movement in the substantially flat portion of the force/deflection curve shown in FIG. 3 is achievable. The flat portion of the curve of FIG. 3 is a constant force region that can be used to produce a constant pressure over a range of displacement volume and is desirable region of operation.

The spring diaphragm 25 can be extended beyond its nested position when assembled such that the spring diaphragm 25 is therefore under stress. The initial displacement is selected to bring the pressure or force exerted by the spring diaphragm 25 to the flat portion of the force/displacement curve illustrated of FIG. 3. Appreciably, the functional volume of the infusion pump 20 is that displacement which takes place over this substantially flat region of the force/deflection curve.

To limit the filling of the infusion pump to a desired displacement of the spring diaphragm 25, a telescoping section 54 can be interconnected to the spring diaphragm 25 and extend into the inlet conduit 32. When the telescoping section 54 is fully extended, collar portion 56 cooperates with a collar portion 58 of the inlet conduit 32 to prevent the spring diaphragm 25 from traveling more than the desired distance. As illustrated, the telescoping section 54 is interconnected to a substantially flat portion 60 of the spring diaphragm. The telescoping section 54, thus limits the stroke of the spring diaphragm 25 as indicated generally by the arrows 62 and causes the filling back pressure to increase rapidly, thereby reducing the risk of damaging the spring diaphragm 25 or causing errors in a drug flow rate due to excess pressure in the drug chamber.

Figure 4:
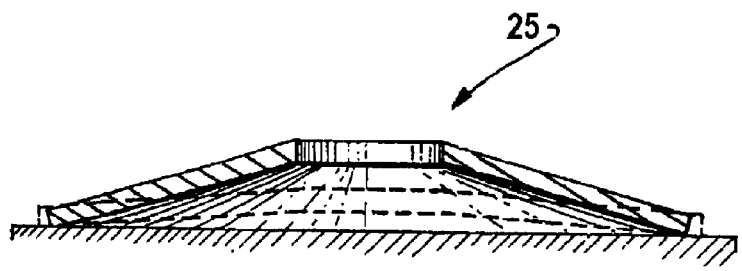
FIG. 4 is a sectional view of one embodiment of a conventional single conical spring-energy source in accordance with the present invention.

An alternative design of the spring diaphragm 25 can take the form of a single Belleville washer, as generally shown in FIG. 4. Not unlike the first spring diaphragm 25 discussed above, a Belleville washer with the proper selection of cone angle and thickness can yield a desired force displacement curve in accordance with FIG. 3. If a strong material like titanium is used, cone height must be very small, i.e., 10 to 20 thousandths of an inch, so as to provide force in the range suitable for infusion pumps, e.g., 4 to 15 psi. This range of heights, which constitutes the effective stroke of a spring diaphragm 35 that includes a single conical spring, is too small to be practical for use in infusion pumps. In order to retain a flat pressure curve and achieve a longer stroke or range of movement of the spring diaphragm 25, a spring material with a lower elastic constant should be used, for example, plastics and elastomers. When low elastic materials are used, the thickness of the conical section can be increased and the cone angle made larger. Accordingly, it is preferred that the spring material used should also have a much greater percent elongation in the elastic region of its stress strain curve. This allows the spring diaphragm 25 to have a much longer range of travel in the substantially flat portion of the curve shown in FIG. 3.

No matter which diaphragm design is employed, it will be appreciated that the shape and thickness of the spring diaphragm 25 may vary in order to exhibit the required force/deflection characteristics.

Figure 5:
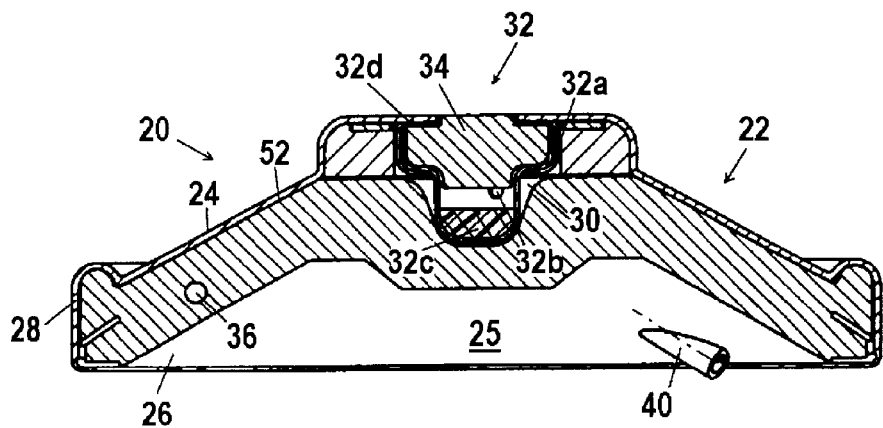
FIG. 5 is a sectional view of an infusion pump in accordance with the present invention.

FIG. 5 illustrates another embodiment of the pump 20 that includes a single conical spring diaphragm 25. The pump 20 of this embodiment is shown in an expended or collapsed state (i.e., substantially no infusate within the fluid chamber 30). In reference to the drawings, the same numerical designations are used to represent like structure between the disclosed embodiments. Accordingly, when this embodiment includes structure substantially identical to that of the embodiment of FIGS. 1 and 2, description of such structure will not be repeated.

The top wall portion 24 offers a simplified configuration over that used for the embodiment shown in FIGS. 1 and 2. Specifically, the top wall portion 24 does not function as a manifold for the outlet passage 36 and related structure, rather the outlet passage 36 is formed in and passes through the spring diaphragm 25. This allows the pump restrictor and delivery catheter connector 40, which is an extension of the outlet passage 36, to be positioned away from the upper surface of the pump 20, thus avoiding the exposure of this sensitive structure from potential damage during a refilling procedure. As will be discussed in greater detail below, this embodiment incorporates a filter system 38 and a flow restrictor 42 within the internalized outlet passage 36.

Figure 12:
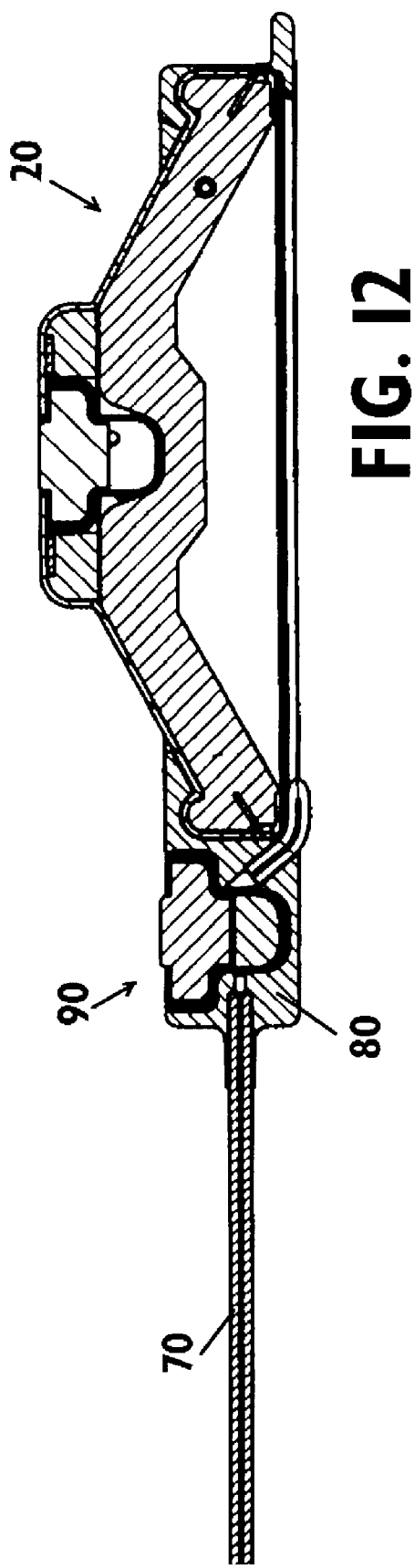
FIG. 12 is a partial sectional view of a pump assembly in accordance with one aspect of the present invention.

For one structural arrangement, the inlet conduit 32 is defined by a needle stop 32a that includes at least one aperture 32b. The needle stop 32a is formed from a hardened material, e.g., stainless steel., titanium, etc. The needle stop 32a receives and holds a resilient material 32c, which serves to effectively stop a needle (not shown) that is inserted through the septum 34 and avoid damage through its contact with the lowest portion of the needle stop 32a. The needle stop 32a is held in place by a retaining structure 32d, which is secured (e.g., welded) to an undersurface of the top wall portion 24. Although FIG. 5 illustrates (and the above description discusses) the use of the resilient material 32c, it should be appreciated that the resilient material 32c is not critical to the present invention, whereas the needle stop 32a can be provided without the resilient material 32c (FIG. 12).

Figure 6A:
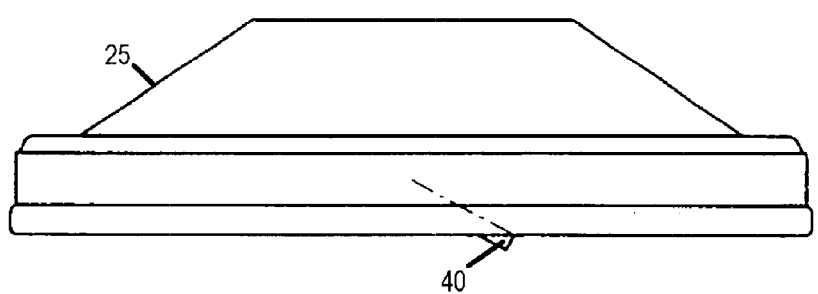
FIG. 6A illustrates a side view of the spring diaphragm for the infusion pump of FIG. 5.
Figure 6B:
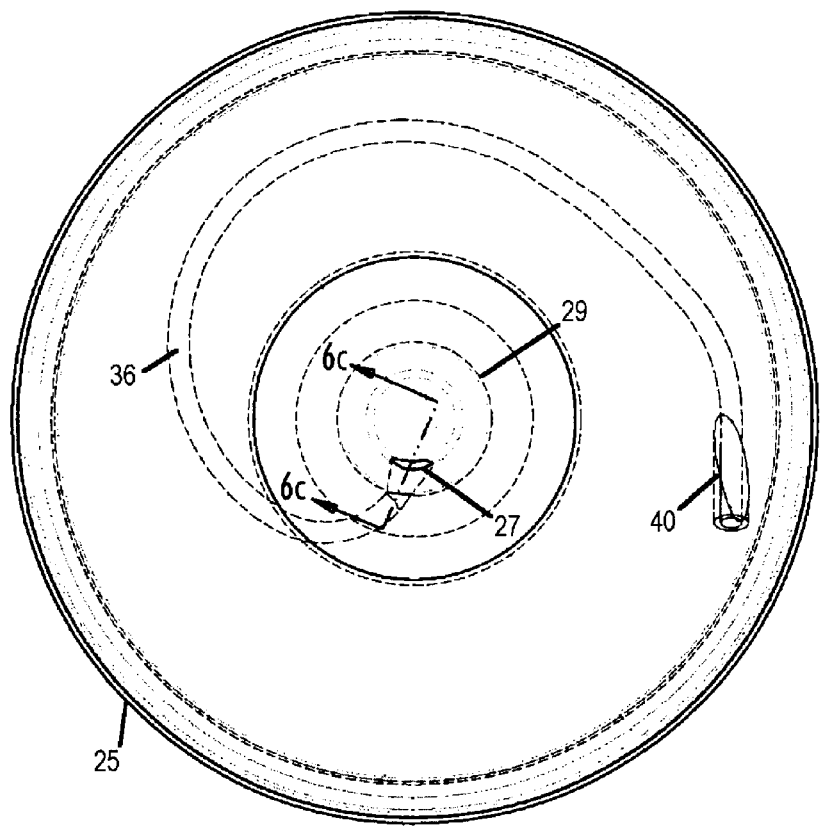
FIG. 6B illustrates a plan view of such spring diaphragm, and FIG. 6C provides a partial sectional view of an inlet to the outlet passage of the spring diaphragm of FIG. 6B taken along line 6C—6C thereof.
Figure 6C:
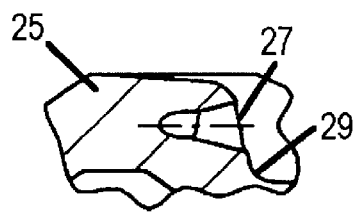

FIGS. 6A and 6B further illustrate the spring diaphragm 25 of this embodiment. FIG. 6A is a side view of the spring diaphragm 25 and is consistent with the sectional view shown in FIG. 5. FIG. 6B is a plan view, which better illustrates the structure of the spring diaphragm 25, including a central portion 29 that can closely receive the needle stop 32a (FIG. 5), the outlet passage 36, the outlet passage inlet 27 (FIG. 6C), and the delivery catheter connector 40.

Operatively, infusate is injected using a needle (not shown) into the inlet conduit 32. The injected infusate passes from the inlet conduit 32 into the fluid chamber 30 via the at least one aperture 32b. Infusate within the fluid chamber 30 enters the outlet passage 36 through the outlet passage inlet 27, which can interface with the aperture 32b in even a collapsed state (see FIG. 6c).

Embedding the outlet passage 36 within the spring diaphragm 25 creates a more compact overall pump design, allows the outlet passage 36 to be made using a basic molding process, and eliminates the need for a separate manifold to house a restrictor and/or filter, such as shown in FIG. 1. Accordingly, this embodiment exhibits greater volumetric efficiency, lower weight, ease of assembly, and requires no substantive change in the overall shape of the pump 20. Moreover, an embedded outlet passage 36 minimizes the occurrence of extreme stretching, compressing, flexing, or kinking of component couplings and joints.

As but one fabrication example, the spring diaphragm 25 is fabricated by first supporting tubing (e.g., silicone tubing) on a flexible mandrel (not shown) within the cavity of a spring mold (not shown). The tubing is selected based largely on its inner diameter—the inner diameter should accommodate a bacteriostatic filter therein but still allow adequate flow thereabout. The mandrel holds the tubing in accordance with a desired shape relative to the final spring diaphragm 25. In this particular example, the mandrel maintains the tubing in a gentle spiral that extends substantially from a top surface of the spring diaphragm (i.e., outlet passage inlet 27) to a position slightly beyond (preferably, 0.1"–1.0") the lower surface thereof (i.e., connector 40). A liquid elastomer (e.g., silicone rubber) is then injected into the mold cavity in and about the supported tubing.

Consequently, the supported tubing is integrated with the spring diaphragm 25 during vulcanization. The flexible mandrel is then removed, thus leaving a hollow tubular channel within the wall of the spring diaphragm 25. The portion of the tubing that extends from the lower surface of the formed spring diaphragm 25 is adapted to be connected to (i) a delivery catheter 70 or (ii) tubing for connection to additional pump structure (e.g., a bolus port).

It should be appreciated that the specific technique utilized to form the internalized outlet passage 36 is not critical to this invention.

As may be seen in both the configurations of FIGS. 2 and 5, it is preferred that an inner surface 52 of the top wall portion 24 be configured to have a somewhat convoluted shape so as to allow the spring diaphragm 25 to nest into the complimentary shape of the inner surface 52. This enables the spring diaphragm 25 to expel substantially all of the drug solution from the fluid chamber 30 during an infusate delivery cycle.

Filtration

As stated before, it is intended that the outlet passage 36 include both a filter 38 and a flow restrictor 42.

In regard to the filter 38, it is a requirement that drug infusion pumps include a means of micro-filtering infusates in order to insure their sterility. While a preferred filter structure would be sintered metal due to its durability, sintered metal filters are not currently available with a micro-filtration pore size. Consequently, filters with sub-micron pore size are conventionally fabricated from organic polymers such as polysulfone, Nylon®, polytetrafluoroethlyene, and cellulose acetate. These organic-based filters are not as durable as metal filters and are more likely to shed particles large enough to partially or completely obstruct some part-of the pump flow path, valve seats, and interstices. Modern implantable infusion pumps have flow paths that range in size from 5 microns to 50 microns.

In addition to the concern of filter break up, it is necessary to filter potentially damaging particles that may be introduced during the manufacturing process. First, silicone rubber, which can be used extensively in the fabrication of the present invention, has the propensity to attract electrostatically charged particles. It is more common than not that silicone rubber parts of the pump 20 will carry and introduce 5–25 micron particles into the pump system that can individually cause device failure. Second, particle control is an issue with respect to the sequence in which the pump 20 is assembled. The microbial filter 38a (e.g., 0.2 micron polysulfone tubular fiber) can be installed within the outlet passage 36 at a relatively early stage of the manufacturing process, but the flow restrictor 42 is fabricated, inspected, and installed at a relatively later stage. The practical concern is that system-harmful particles may be introduced into the pump system, downstream of the microbial filter 38a, despite the strictest of particle control standards and measures.

Figure 7:
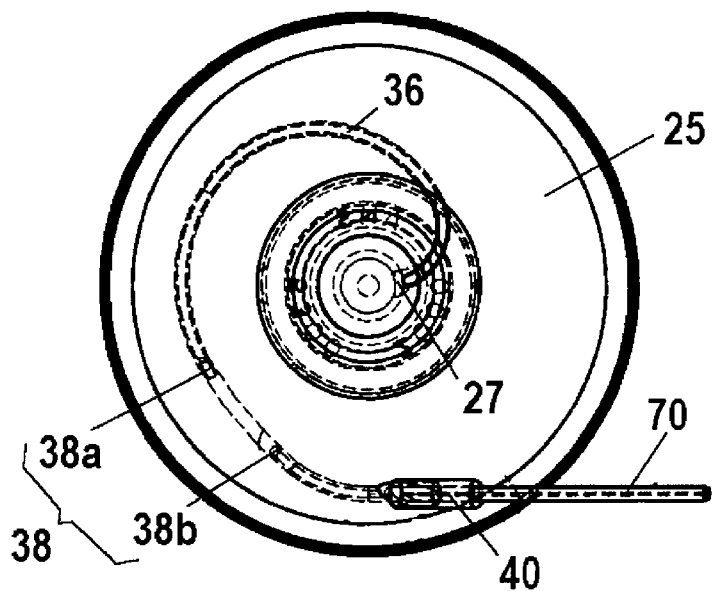
FIG. 7 illustrates a bottom view of the spring diaphragm for the infusion pump of FIG. 5 connected to a delivery catheter.

FIG. 7 illustrates a bottom view of the spring diaphragm 25 of this embodiment, which illustrates the position of both the micro-filter stage 38a and the particle filter stage 38b of the multi-stage filtration system 38, wherein the particle filter stage 38b is downstream of the micro-filter stage 38a. The micro-filter stage 38a is a filter with sub-micron pore size and is preferably fabricated from conventional, organic polymers such as polysulfone, Nylon®, polytetrafluoroethlyene, cellulose acetate, or the like. The particle filter stage 38b is illustrated in FIGS. 8a and 8b.

Figure 8A:
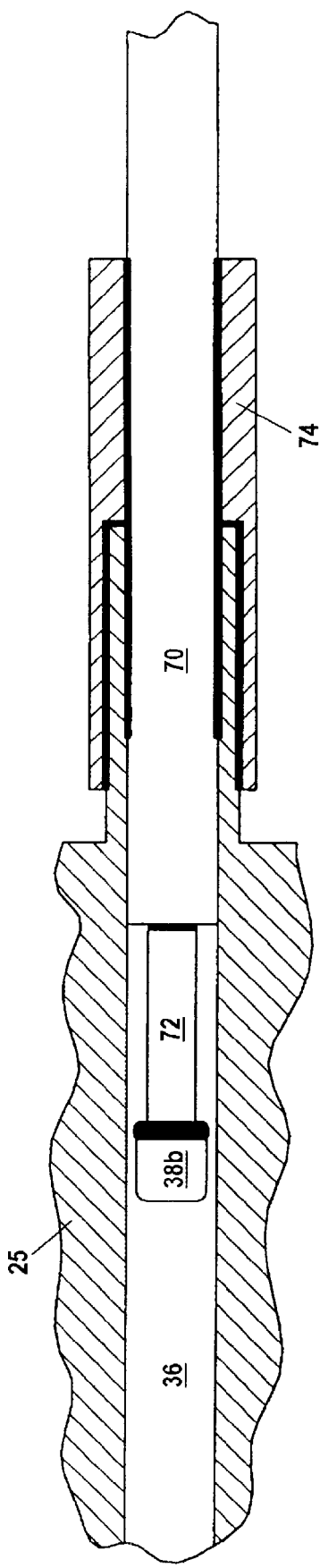
FIGS. 8a and 8b illustrate a second stage of a filter system in accordance with the present invention.

In FIG. 8a, the restrictor 42-particle filter stage 38b assembly is generally shown. In particular, a delivery catheter 70 is positioned through the catheter connector 40 and into the outlet passage 36. The union between the connector 40 and the delivery catheter 70 is reinforced with a sleeve 74. The delivery catheter 70 and/or the sleeve 74 are held in place by an adhesive, friction, mechanical fastener, or the like.

A tubing section 72 extends from a proximal end of the delivery catheter 70. A particle filter 38b is fixed to a proximal end of the tubing section 72 so as to cover the inlet to the lumen of the tubing section 72. While the particle filter 38b can assume any structure capable of preventing at least a 20 micron or greater particle from entering the lumen of the tubing section 72, it is preferred that the particle filter 38b take the form of a sintered, stainless steel mesh. In one embodiment, the mesh of the particle filter 38b is arranged so as to prevent the passage of particles having a size of approximately 20 microns or greater. More preferably, the mesh prevents the passage of particles having a size of approximately 10 microns or greater. Most preferably, however, the mesh prevents the passage of particles having a size of approximately 5 microns or greater. The particle filter 38b is fixed to the tubing section 72 by adhesive, friction, mechanical fasteners, or the like.

Figure 8B:
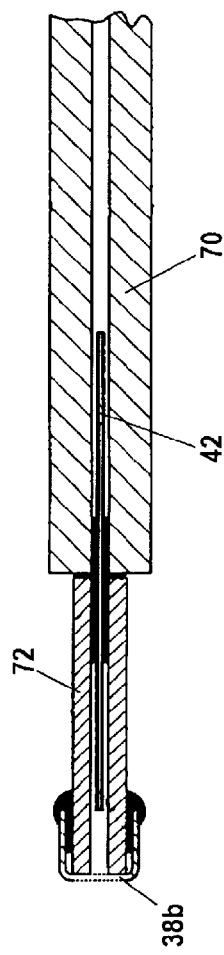

FIG. 8b illustrates a partial sectional view of the structure shown in FIG. 8a. Capillary tubing, or the restrictor 42, shares and extends between the lumens of the delivery catheter 70 and the tubing section 72. Adhesive may be used to fix the relative positions of the delivery catheter 70, tubing section 72, and the restrictor 42. The restrictor 42 is preferably formed from a relatively short length of tubing (e.g., 0.1 cm–3.0 cm) of a prescribed inner diameter (e.g., 10 microns, 15 microns, 20 microns, 25 microns, 30 microns). The restrictor 42 may be fabricated from of a variety of medical grade materials, including silica. Furthermore, it is preferred that a proximal end of the restrictor 42 be treated with trimethychlorosilane or a functionally similar substance.

The concerns of particle control are not limited to the pump 20 of the present invention. Accordingly, the multi-stage filtration system 38 is suitable and particularly applicable to any implantable infusion pump or like device.

SUTURE-SECURING STRUCTURE

At the site of implantation, modern implantable infusion pumps are sutured to nearby tissue to insure their desired placement. Conventional implantable infusion pumps include three or four suture rings (i.e., eyelets), formed of metal or the like, fixed to a side-surface of the respective housings. The suture rings are equally spaced about the housings' perimeter. While suture rings typically offer a suitable means in which to secure an implantable pump, their circumferential placement often constrains pump/suture placement. Accordingly, it is perceived that a need exists for a structure that allows a physician to readily place a suture at largely any position about the pump.

Figure 9:
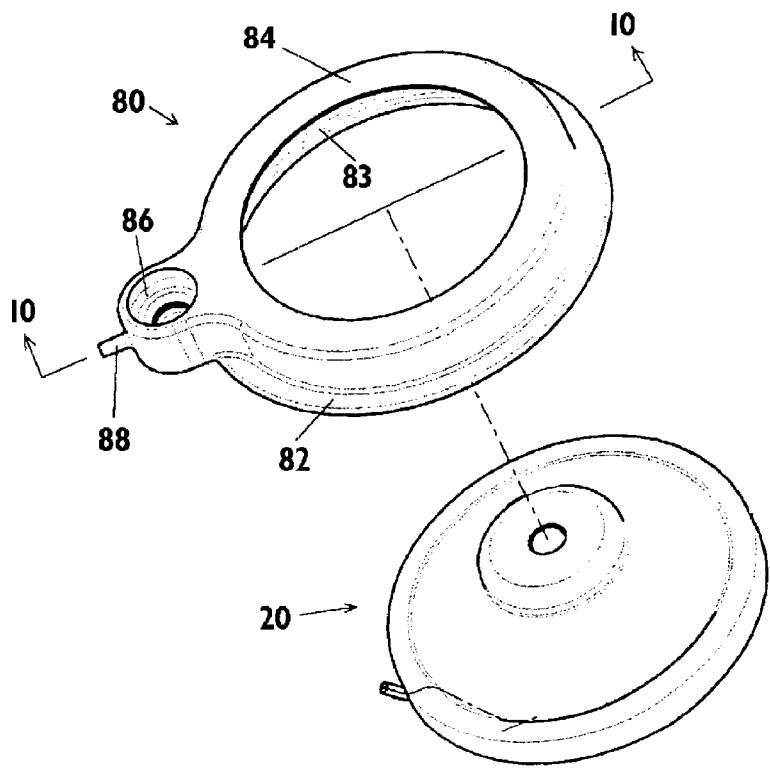
FIG. 9 is a perspective, exploded assembly view of the infusion pump of FIG. 5 and a boot incorporating a suture structure and a bolus port receptacle.

FIG. 9 illustrates an elastomer-reinforced boot 80 in accordance with one aspect of the present invention. The boot 80 has an interior surface 83 that receives the pump 20 and specifically the upper wall portion 24 of the housing-22. The lip 84 of the boot 80 functions to contact the upper-most part of the upper wall portion 24 and insure that the boot 80 is properly positioned relative to the pump 20. Although the boot 80 could function without the lip 84 or the lip 84 could be arranged as to alternatively contact the lower wall portion 26, it is preferred that the lip 84 be configured in accordance with that illustrated in FIGS. 9 and 12. The boot 80 can be fixed to the pump 20 using an adhesive, friction, mechanical fasteners, or the like.

Figure 10:
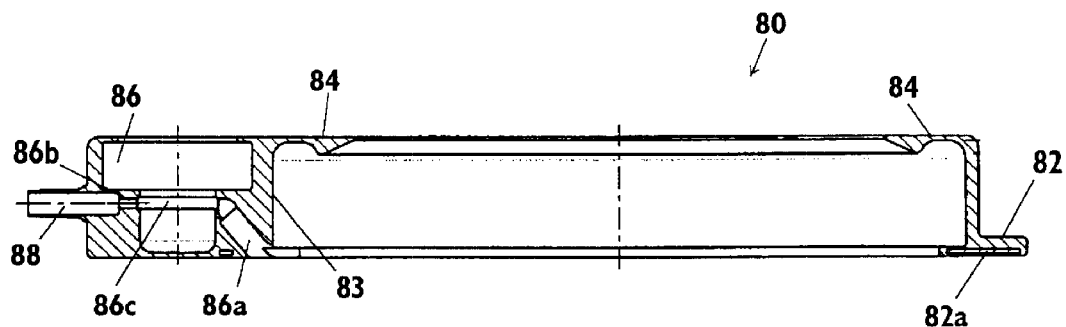
FIG. 10 is a sectional view of the boot of FIG. 9 taken along line 10—10 thereof.

A suture pad 82 extends substantially about the circumference of the boot 80. While the boot 80 is preferably fabricated from a medical grade elastomer, e.g., silicone rubber, silicone rubber cannot alone resist normal forces and stresses concentrated at the sutures sites. Accordingly, a reinforcing material 82a is embedded within the boot 80 (FIG. 10).

In a preferred embodiment, the reinforcing material 82a is a polyester mesh, but it should be understood that the reinforcing material 82a could also be a metal mesh, fabric, or the like. Notwithstanding the "open" structure of these examples, the reinforcing material 82a is preferably encapsulated within the elastomer material of the boot 80 to prevent the in-growth of tissue in the reinforcing material 82a. Otherwise, if the reinforcing material 82a is exposed, tissue can grow in and about such a structure, which could make any pump revision (i.e., replacement) unnecessarily complicated and more traumatic to the surrounding tissue.

While the reinforcing material 82a may certainly be used throughout the entire structure of the boot 80, it is satisfactory and more convenient for fabrication to incorporate the reinforcing material 82a only in the suture pad 82. Moreover, although the suture pad 82 can assume an inclined form (i.e., forming a truncated conical form), embedding the reinforcing material 82a can be more consistently achieved when the suture pad 82 remains substantially flat. The reinforcing material 82a spans continuously (or substantially continuously) about the circumference of the boot 80, thus providing the greatest potential for desirable suture placement.

Figure 11:
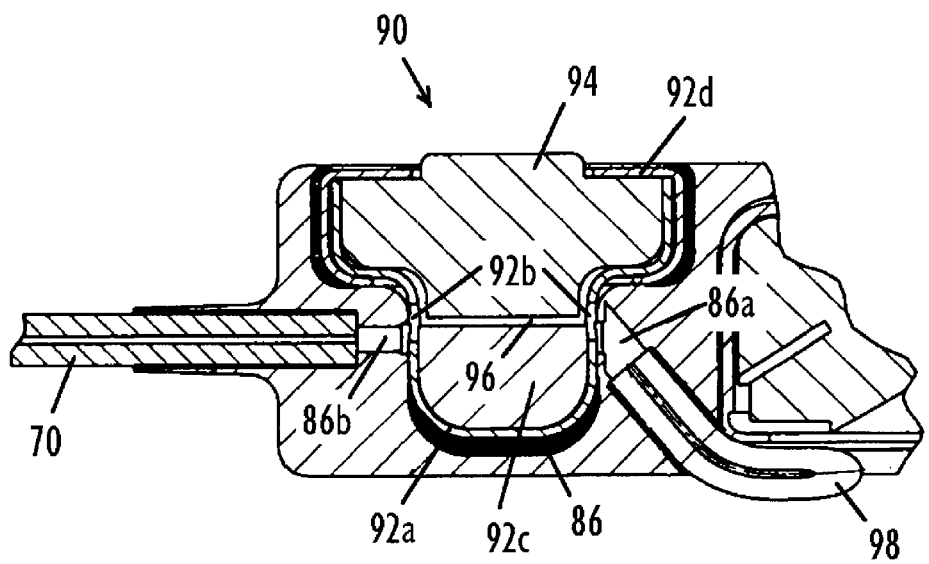
FIG. 11 is a partial sectional view of a bolus port positioned within the bolus port receptacle of the boot of FIGS. 9 and 10.

The illustrated embodiment of the boot 80 includes a bolus port receptacle 86 adapted to receive a bolus port 90. As illustrated in FIG. 11, the bolus port 90 is constructed in a manner generally consistent with the refill port (i.e., inlet conduit 32) of the pump 20. The bolus port 90 is defined by a needle stop 92a that includes at least one aperture 92b. The needle stop 92a is formed from a hardened material, e.g., stainless steel, titanium, etc. The needle stop 92a receives and holds a resilient material 92c, which serves to effectively stop a needle (not shown) that is inserted through the septum 94 and avoid damage through its contact with the lowest portion of the needle stop 92a. A retaining structure 92d holds the septum 94 relative to the needle stop 92a. The bolus port 90 is secured within the bolus port receptacle 86 using adhesive, friction, mechanical fasteners, or the like.

While not critical to the invention, the septum 94 and the resilient material 92c are intended to occupy a significant majority of the volume defined by the needle stop 92a. If this configuration is adopted, this arrangement: (i) minimizes a potential fluid volume within the bolus port 90 and (ii) creates a "keyed" space 96 that can only be accessed by a special needle that has a discharge aperture alignable with the space 96.

The bolus port receptacle 86 of the boot 80 is positioned between, and is in fluid communication with, an inlet 86a and an outlet 86b. A groove 86c is formed in and follows at least a portion of the perimeter of the bolus port receptacle 86. It is preferred that the groove 86c be aligned with the inlet 86a and the outlet 86b, thereby creating a continuous flow path. The groove 86c may be formed about 360° of the interior surface of the receptacle 86 with one aperture 92b formed in the needle stop 92a. Alternatively, the groove 86c may be formed about only 180° of the interior surface of the receptacle 86 with two oppositely positioned apertures 92b formed in the needle stop 92a (FIGS. 10 and 11). Alternatively, to further minimize the potential volume of the groove 86c, the groove 86c may be formed about only 90° of the interior surface of the receptacle 86 with at least two apertures 92b formed in the needle stop 92a. Notwithstanding, for each of the above options, it is possible to have only a single aperture 92b between the bolus port 90 and the groove 86c so as to prevent the possibility of infusate (from the fluid chamber 30) flowing through the bolus port 90.

The bolus port receptacle 86 is connected to the output from pump 20 via a tubing extension 98. The tubing extension 98 extends between the connector 40 and the inlet 86a and is held in place by adhesive, friction, mechanical fasteners, or the like.

While the boot 80 described and illustrated includes a bolus port receptacle 86, it is should be understood that inclusion of the bolus port receptacle 86 is not a requirement of the present invention but an option. Rather, if a bolus port is believed to not be needed for a particular application, the boot 80 can be formed without the receptacle 86. For this configuration, the delivery catheter 70 would be connected directly to the connector 40. Also, it should be further understood that the boot 80 may serve as a medium to collectively arrange a pump and, for example, a bolus port; however, other means or structure other than the suture pad 82 could be provided to enable the assembly to be secured within an implantation site.

While not shown, it should be further appreciated that as an alternative to the boot 80 receiving the pump 20 within an interior surface 83 of the boot 80, at least the suture pad 82 of the boot 80 could be integrated between upper and lower halves of the pump 20.

It will be appreciated that the drug infusion site must be considered in the design of the infusion pump. For example, if the catheter must deliver an infusate into the relatively high pressure of the arterial system, a pump pressure will need to be greater to maintain the same error limits that can be obtained when delivering infusate for other operative purposes, e.g., intravenously, intraperitoneally.

Moreover, although preferred embodiments of the present inventions have been described above, it will be appreciated that other pressure compensating mechanisms in accordance with the principles of the present invention might be utilized. In particular, other constant force spring arrangements might be utilized as an infusate drive source.

It is to be understood that even though the above numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention to the full extent indicated by the broad general meaning of the terms in which the appended claims are expressed.

What is claimed is:

1. An infusion pump having a variable-volume fluid chamber for implantation in a living body, the pump comprising:

a housing;

a driving spring;

an inlet conduit, having a self-sealing penetrable member positioned therein, extends between an outer surface of the housing and the fluid chamber; and an outlet conduit, in communication with the fluid chamber, is adapted to deliver a fluid from the fluid chamber, wherein the self-sealing penetrable member is adapted to be accessible through a surface of a living body when the pump is implanted therein to facilitate provision of a fluid to the fluid chamber, wherein the driving spring is adapted to supply a principle force to drive fluid transiently stored in the fluid chamber into the outlet conduit, and wherein the outlet conduit extends through the driving spring.

2. An infusion pump in accordance with claim 1, further comprising a filter, wherein the filter is positioned within the outlet conduit.

3. An infusion pump in accordance with claim 1, further comprising a flow restrictor, wherein the flow restrictor is positioned within the outlet conduit.

4. An infusion pump in accordance with claim 3, further comprising a filter, wherein the filter is positioned within the outlet conduit.

5. An infusion pump in accordance with claim 1, further comprising a bolus port, wherein the bolus port is in fluid communication with the outlet conduit.

6. An infusion pump in accordance with claim 1, wherein the driving spring is adapted to compensate for changes in internal body pressure when implanted, whereby a pressure differential between the fluid chamber and an internal body pressure remains constant despite changes in body temperature or atmospheric pressure.

7. An infusion pump in accordance with claim 1, further comprising a reinforced-elastomer suture member, fixed relative to the housing, wherein the suture member substantially extends about a perimeter of the housing.

8. An implantable infusion pump having a variable-volume fluid chamber to transiently store a fluid solution, the pump comprising:

a hardened shell structure;

an elastomer spring diaphragm operatively joined to the shell structure, wherein the shell structure and the spring diaphragm cooperate to form the fluid chamber; and a fluid flow passage, in fluid communication with the fluid chamber, is adapted to deliver a fluid solution from the fluid chamber to an infusion site, such passage being substantially embedded within the spring diaphragm, wherein the spring diaphragm is operatively biased toward the shell structure.

9. An infusion pump in accordance with claim 8, wherein the spring diaphragm is adapted to be responsive to an internal body pressure when implanted so as to provide a substantially uniform pressure differential between the fluid chamber and the internal body pressure.

10. An infusion pump in accordance with claim 8, wherein the spring diaphragm is adapted to provide a principal force for forcing a fluid solution from the fluid chamber into the flow passage.

11. An infusion pump in accordance with claim 8, further comprising a filter, wherein the filter is positioned within the flow passage.

12. An infusion pump in accordance with claim 8, further comprising a filter system having multiple stages, each stage being responsible for filtering an embolus of a prescribed characteristic, and the filter system is positioned within the flow passage.

13. An infusion pump in accordance with claim 12, wherein the filter system comprises a micro-filter stage and a particle-filter stage, the particle-filter stage being positioned downstream of the micro-filter stage.

14. An infusion pump in accordance with claim 8, further comprising a flow restrictor, wherein the flow restrictor is positioned within the flow passage.

15. An infusion pump in accordance with claim 8, further comprising a bolus port, wherein the bolus port is in fluid communication with flow passage.

16. An infusion pump in accordance with claim 8, further comprising a reinforced-elastomer suture member, fixed relative to the shell structure, wherein the suture member substantially extends about a perimeter of the shell structure.

17. An infusion pump in accordance with claim 8, further comprising a boot member adapted to receive and to encompass at least a portion of the shell structure.

18. An infusion pump in accordance with claim 17, further comprising a bolus port, wherein the boot member further includes a bolus port receptacle that receives the bolus port, and the bolus port receptacle is in fluid communication with the bolus port, an output connectable to a delivery catheter, and the outlet passage.

19. An infusion pump in accordance with claim 17, wherein the boot member includes a suture member, and the suture member substantially extends about a perimeter of the shell structure.

20. An infusion pump for implantation in a living body, the pump comprising:

a housing defining a portion of a collapsible fluid-tight chamber;

a moveable spring diaphragm, defining another portion of the chamber, adapted to (i) exert a force on a solution stored in the chamber and (ii) compensate for changes in body pressure by communicating such changes to the chamber;

an inlet conduit, having a self-sealing, penetrable member, extending between an exterior surface of the housing and the chamber;

an outlet conduit in fluid communication with the chamber and an infusion site in the body, wherein at least a portion of the outlet conduit passes through the spring diaphragm; and a reinforced-elastomer suture structure, extending substantially continuously about a perimeter of the pump, adapted to receive and to retain a suture placed along substantially an entire length of the suture structure.

21. An infusion pump for implantation in a living body, the pump comprising:

a housing defining a portion of a collapsible fluid-tight chamber;

a moveable spring diaphragm, defining another portion of the chamber, adapted to (i) exert a force on a solution stored in the chamber and (ii) compensate for changes in body pressure by communicating such changes to the chamber;

an inlet conduit, having a self-sealing, penetrable member, extending between an exterior surface of the housing and the chamber; and an outlet conduit in fluid communication with the chamber and an infusion site in the body, wherein at least a portion of the outlet conduit passes through the spring diaphragm.

22. An infusion pump for implantation in a living body, the pump comprising:

a housing defining a collapsible fluid chamber to transiently store infusate;

an outlet conduit, in communication with the fluid chamber, is adapted to deliver infusate to a delivery site; and a multi-stage filter system, positioned within the outlet conduit, to filter infusate prior to its delivery to the delivery site.

23. An infusion pump in accordance with claim 22, further comprising a flow restrictor, wherein the flow restrictor is positioned downstream of the filter system.

24. An infusion pump in accordance with claim 22, wherein the filter system includes:
   a micro-filter stage to filter sub-micron emboli from the infusate; and
   a particulate filter stage to filter particles greater than 1 micron from the infusate, wherein the particulate filter stage is positioned downstream from the micro-filter stage.

25. An infusion pump for implantation in a living body, the pump comprising:
   a housing defining at least a portion of a variable-volume fluid chamber to receive an infusate;
   an inlet conduit, having a self-sealing penetrable member positioned therein, positioned at a surface of the housing and being in communication with the fluid chamber;
   an outlet conduit in communication with the fluid chamber and connectable to a delivery catheter;
   a flow restrictor, positioned between the fluid chamber and the delivery catheter;
   a first filter stage, positioned prior to the flow restrictor; and
   a second filter stage, interpositioned between the first filter stage and the flow restrictor.

26. An infusion pump in accordance with claim 25, wherein the first filter stage is adapted to filter sub-micron emboli from an infusate.

27. An infusion pump for implantation in a living body, the pump comprising:
   a housing having a collapsible fluid chamber to transiently store infusate and an energy source to collapse the fluid chamber;
   an inlet conduit, having a self-sealing penetrable member positioned therein, located at a first position relative to the housing and in communication with the fluid chamber;
   an outlet conduit, in communication with the fluid chamber, adapted to deliver infusate to a delivery site; and
   a member having:
      a first mating surface to receive the housing; and
      a reinforced-elastomer suture structure, extending substantially about a perimeter of the member, adapted to receive and maintain sutures applied to secure the pump at an implantation site.

28. An infusion pump for implantation in a living body, the pump comprising:
   a housing having a collapsible fluid chamber to store infusate and an energy source to collapse the fluid chamber;
   an inlet conduit, having a self-sealing penetrable member positioned therein, located at a first position relative to the housing and in communication with the fluid chamber;
   an outlet conduit, extending between the fluid chamber and an output aperture;
   a bolus port, which includes a self-sealing penetrable member;
   a boot structure having:
      a first mating surface to receive the housing; and
      a bolus port receptacle, having an inlet passage and an outlet passage, to receive the bolus port, wherein the outlet passage is adapted to deliver infusate to a delivery site; and
   a connection conduit to extend between the inlet of the bolus port receptacle and the output aperture of the outlet conduit.

29. A pump in accordance with claim 28, wherein the member further comprises a reinforced-elastomer suture structure, extending substantially about a perimeter of the member, to receive and maintain sutures applied to secure the pump at an implantation site.

30. A pump in accordance with claim 28, wherein the bolus port receptacle includes a path connecting the inlet passage and the outlet passage, and the path enables fluid communication between the inlet passage and the outlet passage when the bolus port receptacle receives a bolus port.

* * * * *